United States Patent [19]

Johnson et al.

[11] 4,304,568
[45] Dec. 8, 1981

[54] MINIMIZING OZONE FADING IN DYED POLYAMIDES BY TREATING SAME WITH SUBSTITUTED PIPERIDINE THIOUREAS

[75] Inventors: David A. Johnson, Norton, Mass.; Robert L. Lilly, Asheville, N.C.

[73] Assignee: Akzona Incorporated, Asheville, N.C.

[21] Appl. No.: 151,235

[22] Filed: May 19, 1980

[51] Int. Cl.³ .............. D06P 1/642; C08L 5/34; D06P 5/02; B32B 27/02
[52] U.S. Cl. .............................. 8/568; 8/585; 260/45.8 N
[58] Field of Search ............... 8/568, 585, 442; 260/45.8 N; 428/474

[56] References Cited

U.S. PATENT DOCUMENTS

| | | | |
|---|---|---|---|
| 3,584,993 | 6/1971 | Myles et al. | 8/585 |
| 3,705,166 | 12/1972 | Murayama et al. | 260/37 R |
| 3,822,996 | 7/1974 | Lofquist et al. | 8/585 |
| 3,828,052 | 8/1974 | Holt et al. | 260/293.62 |
| 3,904,581 | 9/1975 | Murayama et al. | 260/45.8 N |
| 3,917,449 | 11/1975 | Wells et al. | 8/495 |
| 4,105,404 | 8/1978 | Lofquist et al. | 8/643 |

FOREIGN PATENT DOCUMENTS 51-88795  8/1976  Japan ........................... 8/442

Primary Examiner—Maria P. Tungol
Attorney, Agent, or Firm—Francis W. Young; Jack H. Hall

[57] ABSTRACT

There is disclosed a method for minimizing ozone fading in dyed polyamides by treating the dyed polyamide with a substituted piperidine thiourea of the formula

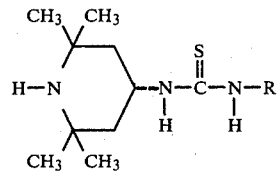

where R is a lower alkyl radical having 1–5 carbon atoms or phenyl. The treated dyed polyamides, preferably in fiber form, display minimize ozone fade without a reduction in light stability.

16 Claims, No Drawings

MINIMIZING OZONE FADING IN DYED POLYAMIDES BY TREATING SAME WITH SUBSTITUTED PIPERIDINE THIOUREAS

BACKGROUND OF THE INVENTION

1. Field of the Invention

The present invention relates to a method of treating dyed polyamides to minimize ozone fading thereof. More particularly, the invention relates to a method of treating dyed polyamides with a substituted piperidine thiourea derivative so that the dyed polyamide, particularly one dyed with a disperse dyestuff, will have minimized or reduced ozone fading without a reduction in light stability.

2. Discussion of the Prior Art and Other Information

Salvin and Walker reported in 1955 the phenomenon of ozone fading of dyes in fiber. Textile Res. Journal, Vol. 25, p. 571. Since that time it was determined that nylon fibers dyed with disperse dyes, particularly Disperse Blue 3, C.I. No. 61505 are quite susceptible to ozone fading when the dyed fiber is subjected to high temperatures and humidity.

Ozone is ordinarily present in air at sea level at concentrations of about 1 to 5 parts per one hundred million. Although ozone is present in this extremely low concentration, a disperse dyed fiber will undergo severe ozone fading if the humidity in the atmosphere is high enough, i.e., over 75% relative humidity.

Various attempts have been made to overcome the problem of ozone fading by using certain disperse dyes. However, this technique is not always effective and can give rise to other problems such as increased processing costs and unlevel dyeing. A search has been undertaken to develop chemicals known as antiozonants to improve the dye ozone fastness of polyamides. While some chemicals improve the ozone fastness of polyamide fibers, many of the chemicals greatly reduce the light stability of the fibers. These chemicals include 4-benzyl-thiosemicarbazide, 4-t-butylthiosemicarbazide, 4,4-dimethyloxazoline-2-thiol, 1-(2-hydroxyethyl)-3-methylthiourea, 1-t-butyl-3-(2-hydroxyethyl) thiourea, 1-(2-hydroxyethyl)-3-phenylthiourea, 1-n-butyl-3-(2-hydroxymethyl-2-propyl)thiourea, 1-(1,3-dihydroxy-2-methyl-2-propyl)-3-phenyl-thiourea, 2,5-bisoctyldithio-1,3,4-thiodiazole, 2,5-dimercapto-1,3,4-thiodiazole, N,N-diethylthiourea, 2,4-dihydroxybenzophenone, 4-dodecyloxyhydroxybenzophenone, 2,4-dimethylbenzophenone, t-butyl-diethanolamine, a mixture of tannic acid and tartar, 2-hydroxy-4-methoxybenzophenone-5-sulfonic acid, and oxalic anilide.

A list of various gas fade inhibitors, including symmetrical diphenyl substituted thioureas, appear in the American Dyestuff Reporter, May 12, 1952 at page 300 as part of an article by Salvin et al. entitled "Advance in Theoretical and Practical Studies of Gas Fading." The article states that the fiber and the dye both play a part in gas fading caused by nitrogen dioxide.

U.S. Pat. No. 3,822,996 to Lofquist et al teaches the use of a water-soluble thiourea for coating dyed nylon fibers to give an improved resistance to ozone fading. The water-soluble thiourea is a saturated alkyl substituted thiourea having less than 5 carbon atoms such as dimethyl thiourea, trimethyl thiourea, and N-methyl thiourea.

Various polythioureas to inhibit ozone fading of dyed polyamides are disclosed in U.S. Pat. No. 3,917,449 to Wells et al. These compounds have the general formula

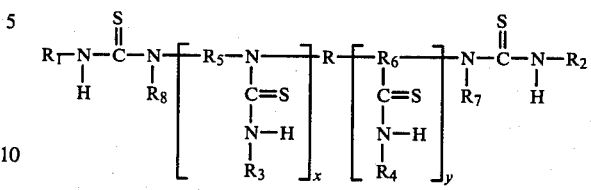

where x and y are 0, 1, or 2, R is a difunctional aliphatic hydrocarbon radical or

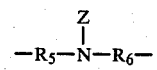

where Z is H or

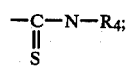

$R_1$, $R_2$, $R_3$, and $R_4$ are independently selected from phenyl or a monofunctional allyl or alkyl radical of 1 to 12 carbon atoms, $R_5$ and $R_6$ are

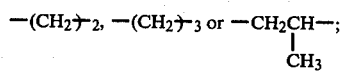

$R_7$ and $R_8$ are independently H or monofunctional ally or alkyl of 1 to 12 carbon atoms with the proviso that when x=0 and $R_1$ and $R_2$ are allyl, R has to be a difunctional fatty acid residue of 24 to 108 carbon atoms or a difunctional alkyl substituted cyclic aliphatic hydrocarbon.

U.S. Pat. No. 3,705,166 to Murayama et al. discloses acrylic acid derivatives of 2,2,6,6,-tetramethyl-piperidines useful as stabilizers for the photo- and thermal deterioration of various synthetic polymers, including polyamides.

U.S. Pat. No. 3,828,052 to Holt et al describes acylhydrazone derivatives of 2,2,6,6,-tetramethyl piperidine-4-one as stabilizers of organic materials. The derivatives are said to be particularly worthwhile to stabilize polyolefins against the effects of ultra-violet radiation. The derivatives are said to be generally light stabilizers.

U.S. Pat. No. 3,584,993 to Myles et al. shows alkylene bis-allyl thioureas as stabilizing agents for disperse dyes and nylon. The thioureas are generally nitrogen substituted N-allylthioureas.

U.S. Pat. No. 3,904,581 to Murayama et al. relates to the stabilization of synthetic polymer against photo and thermal deterioration by incorporating various alkyl substituted piperidines therein.

GENERAL DESCRIPTION OF THE INVENTION

It has now been found that dyed polyamides can have a minimized ozone fade by treating the dyed polyamide with a substituted piperidine thiourea of the formula:

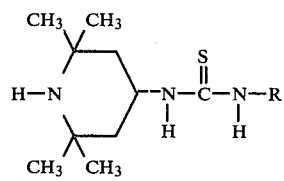

where R is lower alkyl with up to 5 carbon atoms or phenyl. The substituted piperidine thioureas can be incorporated or coated on polyamide fibers in a quantity sufficient to minimize or reduce ozone fading. The substituted piperidine thiourea is preferably added in a quantity of about 0.5 to 1% by weight based on the amount of the polyamide on the polyamide.

Although the dyed polyamides have a minimized ozone fade, there is no reduction in light stability, which is a disadvantage of many anti-ozonants of the prior art.

PREFERRED EMBODIMENTS OF THE INVENTION

The polyamide used in the present invention is a polyamide capable of being formed into a fiber, preferably nylon 6 or nylon 66. Both aliphatic and aromatic polyamides can be used in the present invention.

The polyamide can be dyed with a disperse dye such as Disperse Blue 3. Other disperse dyes include C.I. Basic Blue 47 (Astrazon Blue 3 RL) and C.I. Disperse Blue 7 (Celliton Blue-Green BA). It seems that the most sensitive dyes are anthraquionone based, particularly blue dyes with an anthraquinone nucleus.

It is also possible to treat the polyamide before dyeing and use the resulting product as an intermediate material for final dyeing and which will possess a built-in resistance to ozone fading. The substituted piperidine thioureas can be incorporated in the spin finish, in the over-finish prior to dyeing or sprayed in solutions onto a dyed polyamide.

The substituted piperidine thiourea derivatives used in the present invention can be made in accordance with the techiques described in U.S. Pat. No. 3,904,581. The reactions generally involve the reaction of amino piperidines with substituted isothiocyanates; see Examples 1 to 3, infra.

EXAMPLE 1

Synthesis of 1-phenyl-3-(2,2,6,6-tetramethyl-4-piperidyl)thiourea

Into a 50 ml three-neck round bottom flask were placed 5 g of 4-amino-2,2,6,6-tetra-methyl piperidine in 10 ml of dry spectra grade acetone. The reaction flash was then equipped with a small magnetic stirring bar and reflux condenser. A 100 ml addition funnel containing 4.32 g of phenyl isothiocyanate in 20 ml of acetone was placed in the reaction flask. The addition of phenyl isothiocyanate was exothermic and was completed in 1 hour. The reaction solutin was heated at reflux for 2 hours under a dry nitrogen purge, and then cooled to room temperature. The yellow-green solution was evaporated to dryness and the yellow solid was recrystallized from (20/80) acetone/H₂O. The recrystallized product was a white solid, m.p. 174° C., yield 7.2 g, 77%.

Similar techniques can be used for the production of 1-ethyl-3-(2,2,6,6-tetramethyl-4-piperidyl)thiourea and 1-butyl-3-(2,2,6,6-tetramethyl-4-piperidyl)thiourea. See the following two examples.

EXAMPLE 2

Synthesis of 1-butyl-3-(2,2,6,6-tetramethyl-4-piperidyl)thiourea

Amino-piperidine (5 g) in 20 ml benzene was placed in a 50 ml three-neck round bottom flask equipped with a magnetic stir bar and a reflux condenser. A 100 ml addition funnel containing 3.68 g. of N-butyl isothiocyanate in 20 ml benzene was added slowly to the flask. The addition was completed in 30 minutes. The reaction product was recrystallized from benzene to give 6.95 g of 1-butyl-3-(2,2,6,6,-tetramethyl-4-piperidyl)thiourea; 80% yield. m.p. 100°–120° C. The structure was supported by IR and NMR spectra. Elemental analysis:

|   | Found (%) | Calculated (%) |
|---|-----------|----------------|
| C | 62.23     | 61.94          |
| H | 11.38     | 11.42          |
| N | 15.44     | 15.47          |

EXAMPLE 3

Synthesis of 1-ethyl-3-(2,2,6,6-tetramethyl-4-piperidyl)thiourea

Into a 50 ml three-neck round bottom flask there was placed 5 g of amino-piperidine in 20 ml benzene. The flask was equipped with a magnetic stir bar and a reflux condenser. A 100 ml addition funnel containing 2.78 g of N-ethyl isothiocyanate in 10 ml benzene was slowly added to the flask. The reaction was slightly exothermic and was refluxed for 2 hours. After cooling to room temperature, a white solid precipitated. The solid was filtered and the liquid residue was chilled and filtered. The solid products were combined and recrystallized from chilled benzene to give 7.0 g of 1-ethyl-3-(2,2,6,6-tetramethyl-4-piperidyl)thiourea; 90% yield. m.p. 134° C. The structure was supported by IR and NMR spectra. Elemental analysis:

|   | Found (%) | Calculated (%) |
|---|-----------|----------------|
| C | 59.66     | 59.21          |
| H | 11.26     | 11.18          |
| N | 17.20     | 17.26          |

EXAMPLE 4

This example is directed to ozone fade minimization of dyed polyamides.

Test fabric (knit tubes) were knit on a circular knitting machine from 2500/136 nylon 6 carpet yarn (Clemson M-2011). The knit tubes were autoclaved before dyeing. After autoclaving, the tubes were dyed in the following manner.

All dyeings were carried out in closed stainless steel beakers, which were rotated in an aqueous bath of a standard model AATCC Atlas Launder-Ometer.
30/1 Bath Ratio
  Set bath cold with:
  0.33 g/l Merpol HCS
  0.83 g/l Trisodium Phosphate
  0.33 g/l Celliton Fast Blue FFRN ex. conc. (Disperse BLue 3)

The temperature of the bath was raised to 95° C. (205° F.) during a 45-minute period and dyeing was carried out for 1 hour at 95° C. The fabric was rinsed with hot and cold water (5 minutes each) followed by extraction of excess water and air drying.

The knit tubes were cut into sections about 12 inches long and each section was weighed. The tubes were weighed and then sprayed using a hand-operated spray gun to apply various solutions of substituted piperidine thioureas at 30% pickup to a fabric (i.e. knit tubes which have been cut to make flat fabrics). The fabric was weighed before and after spraying to determine the amount of moisture and thus the quantity of antiozonant applied from each solution. This was based on the difference in weight between the coated and the uncoated tubes, compared to an untreated control.

The tubes were dried and heat-set in a laboratory oven at 145° C. for 10 minutes. The tubes were tested for colorfastness to ozone by A.A.T.C.C. Test Method 129-1972, "Colorfastness to Ozone in the Atmosphere under High Humidities". The test conditions were: 50 pphm ozone, 85% RH, 104° F./40° C. for 8 and 16 hours. The tubes were tested for colorfastness to light according to the procedure described in AATCC Test Method 16A-1974 "Colorfastness to Light: Carbon-Arc Lamp, Continuous Light", using a carbon-arc lamp fading apparatus. Samples were exposed for 40 and 80 hours. Fading rates ($\Delta E$) were determined from L, a, and b values measured with a Hunter Color Difference Meter.

$$\Delta E = [(L_1-L_2)^2 + (a_1-a_2)^2 + (b_1-b_2)^2]^{\frac{1}{2}}$$

The results are listed in Table I

TABLE I

Fading Rates of Treated Samples ($\Delta E_s$) and Untreated Controls ($\Delta E_c$) and Ratios of Their Fading Rates ($\Delta E_s/\Delta E_c$)

| | Ozone-Light Exposure Time (Hours) | | | | | | | |
|---|---|---|---|---|---|---|---|---|
| | $\Delta E$ Values | | | | Ratios $\Delta E_s/\Delta E_c$ | | | |
| | Ozone | | Light | | Ozone | | Light | |
| | 8 | 16 | 40 | 80 | 8 | 16 | 40 | 80 |
| 1-phenyl-3-(2,2,6,6-tetra-methyl-4-piperidyl) thiourea | | | | | | | | |
| 0.5% (on weight of yarn) | 5.1 | 11.0 | 13.8 | 17.4 | 0.27 | 0.28 | 0.87 | 0.77 |
| 0.75% (on weight of yarn) | 9.0 | 28.1 | 12.0 | 17.6 | 0.47 | 0.72 | 0.76 | 0.78 |
| 1-butyl-3-(2,2,6,6-tetra-methyl-4-piperidyl) thiourea | | | | | | | | |
| 0.5% (on weight of yarn) | 5.5 | 11.6 | 14.7 | 16.3 | 0.29 | 0.30 | 0.93 | 0.72 |
| 1-ethyl-3-(2,2,6,6-tetra-methyl-4-piperidyl-thiourea | | | | | | | | |
| 0.5% (on weight of yarn) | 6.5 | 14.6 | 11.7 | 13.4 | 0.34 | 0.37 | 0.74 | 0.59 |
| 0.75% (on weight of yarn) | 3.4 | 14.9 | 10.6 | 15.1 | 0.18 | 0.38 | 0.67 | 0.67 |
| Untreated Control (methanol) | 19.0 | 39.3 | 15.8 | 22.6 | — | — | — | — |
| Untreated Control (hexane) | 29.1 | 40.2 | | | | | | |

What is claimed is:

1. A method of minimizing ozone fading in a dyed polyamide without reducing the light stability of the dyed polyamide comprising:
   treating a dyed polyamide with an ozone fade minimizing effective amount of a substituted piperidine thiourea of the formula:

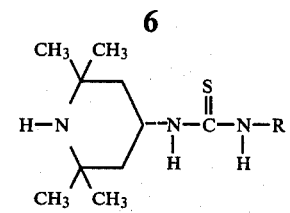

wherein R is selected from the group consisting of lower alkyls having from 1 to 5 carbon atoms and phenyl.

2. The method of claim 1, wherein said dyed polyamide is a dyed polyamide fiber.

3. The method of claim 2, wherein said dyed polyamide fiber is a dyed nylon 6 fiber.

4. The method of claim 2, wherein said dyed polyamide fiber is a disperse dyed polyamide fiber.

5. The method of claim 4, wherein said disperse dyed polyamide fiber is a Disperse Blue 3 dyed polyamide fiber.

6. The method of claim 1, wherein said dyed polyamide is dyed nylon 6.

7. The method of claim 1, wherein said substituted piperidine thiourea is present in an amount sufficient to impart same in a quantity of about 0.5 to about 1% by weight of said dyed polyamide on said polyamide.

8. The method of claim 1, wherein R is phenyl.

9. The method of claim 1, wherein R is butyl.

10. The method of claim 1, wherein R is ethyl.

11. The method of claim 1, wherein said dyed polyamide is an anthraquinone dyed polyamide.

12. Dyed polyamide treated in accordance with the method of claim 1.

13. A polyamide fiber having incorporated therein an ozone fade reducing quantity of a substituted piperidine thiourea of the formula:

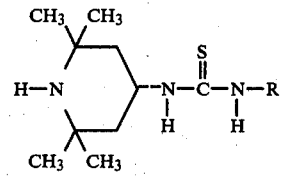

wherein R is selected from the group consisting of lower alkyls having from 1 to 5 carbon atoms and phenyl.

14. The polyamide fiber of claim 13, wherein R is ethyl.

15. The polyamide fiber of claim 13, wherein R is butyl.

16. The polyamide fiber of claim 13, wherein R is phenyl.

* * * * *